(12) United States Patent
Cembrowski

(10) Patent No.: US 9,439,590 B2
(45) Date of Patent: Sep. 13, 2016

(54) METHOD AND APPARATUS FOR BLOOD COLLECTION

(71) Applicant: George S. Cembrowski, Edmonton (CA)

(72) Inventor: George S. Cembrowski, Edmonton (CA)

( * ) Notice: Subject to any disclaimer, the term of this patent is extended or adjusted under 35 U.S.C. 154(b) by 36 days.

(21) Appl. No.: 13/800,857

(22) Filed: Mar. 13, 2013

(65) Prior Publication Data
US 2014/0261872 A1    Sep. 18, 2014

(51) Int. Cl.
*B01L 3/14* (2006.01)
*A61B 5/15* (2006.01)
*A61B 5/157* (2006.01)
*A61M 1/36* (2006.01)
*G01N 33/49* (2006.01)

(52) U.S. Cl.
CPC ......... *A61B 5/15003* (2013.01); *A61B 5/1405* (2013.01); *A61B 5/157* (2013.01); *A61B 5/15087* (2013.01); *A61B 5/150351* (2013.01); *A61B 5/150755* (2013.01); *A61M 1/3633* (2013.01); *A61B 5/150786* (2013.01); *G01N 33/49* (2013.01)

(58) Field of Classification Search
CPC .............. B01L 3/5021; B01L 3/5082; B01L 2300/02; B01L 2300/021; B01L 2300/024; B01L 2300/025; B04B 5/0414; A61B 5/150351; A61B 5/150755; A61B 5/150786; G01N 33/49

USPC ........ 116/201, 203, 212, 215; 422/547, 548, 422/549, 568
See application file for complete search history.

(56) References Cited

U.S. PATENT DOCUMENTS

2010/0032437 A1*   2/2010  Lossau ........................ 220/694
2011/0313684 A1*  12/2011  Furrer et al. .................... 702/41

OTHER PUBLICATIONS

"BD Vacutainer: Evacuated Blood Collection System", Product Insert, Becton, Dickinson and Company, Franklin Lakes, NJ. Obtained from the Internet: <URL: https://www.bd.com/vacutainer/pdfs/VDP40161.pdf>, (2015), p. 1-5.

* cited by examiner

*Primary Examiner* — Jill Warden
*Assistant Examiner* — Dwayne K Handy
(74) *Attorney, Agent, or Firm* — Schwegman Lundberg & Woessner, P.A.

(57) ABSTRACT

Blood collection apparatus includes a blood collection container and a mix detection unit operatively coupled to the blood collection container. The mix detection unit includes a device to produce a data signal indicative of the extent to which the blood collection container is moved in a manner to promote mixing of blood collected into the container and an anti-coagulant also present in the container. A method described herein provides for filling a blood collection container with blood, inverting the blood collection container by hand to mix the blood with an anti-coagulant, and viewing or listening to an indication generated by a mix detection device attached to the blood collection container, wherein the indication provides information about the appropriate amount or mixing for the blood.

11 Claims, 3 Drawing Sheets

METHOD AND APPARATUS FOR BLOOD COLLECTION

TECHNICAL FIELD

This technology relates to blood collection in general and more particularly to blood collection methods and apparatus.

BACKGROUND

Each day, worldwide, hundreds of thousands of patients visit blood collection centers for the purpose of getting their blood sampled for eventual or immediate diagnostic testing. During a patient visit, the phlebotomist punctures the patient's superficial vein (usually an arm vein) with a hollow needle and blood is aspirated into evacuated plastic or glass tubes. These plastic or glass tubes usually contain anticoagulants or procoagulants, compounds that are placed as liquid into the blood collection tube or sprayed onto the inside surface of the tube. For these anticoagulants (or procoagulants) to work properly, the fresh incoming blood must be adequately mixed with the anti- or pro-coagulant. In the absence of mixing or because of insufficient mixing, the incompletely reacted blood can form clots that can result in the malfunction of the blood analyzer (including plugging) or an incorrect analysis of the blood specimen leading to diagnostic errors and delays in diagnosis. One example of insufficient mixing causing misdiagnosis is falsely elevated troponin (an indicator of myocardial infarction) in plastic blood tubes containing the anticoagulant lithium heparin. Moreover, despite continuingly reminding blood drawing staff to mix their blood tubes after drawing, the inversion step constitutes only one of a great many steps in the typical phlebotomy process, and there are considerable external and internal pressures that hurry the phlebotomist.

BRIEF DESCRIPTION OF THE DRAWINGS

The accompanying figures, in which like reference numerals refer to identical or functionally-similar elements throughout the separate views and which are incorporated in and form a part of the specification, further illustrate the present technology and, together with the detailed description of the technology, serve to explain the principles of the present technology.

DETAILED DESCRIPTION

Figure 1:
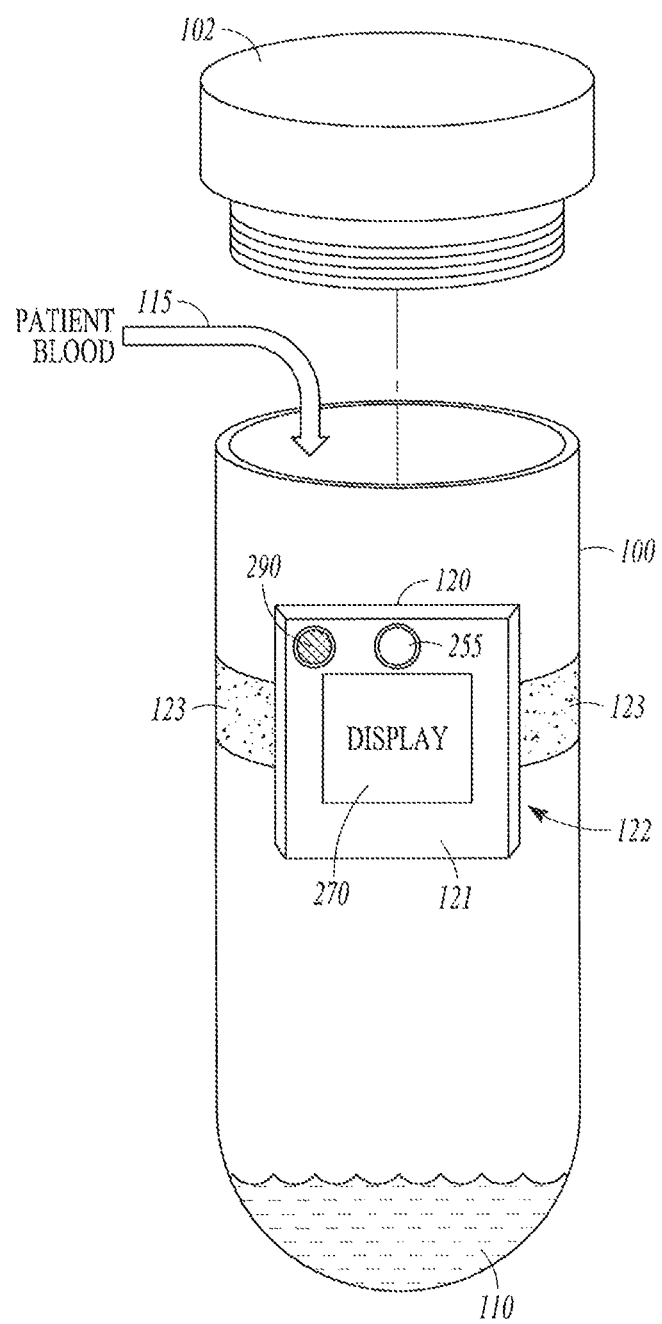
FIGS. 1, 2A, 2B and 3 illustrate blood collection apparatus according to the present technology.
Figure 2A:
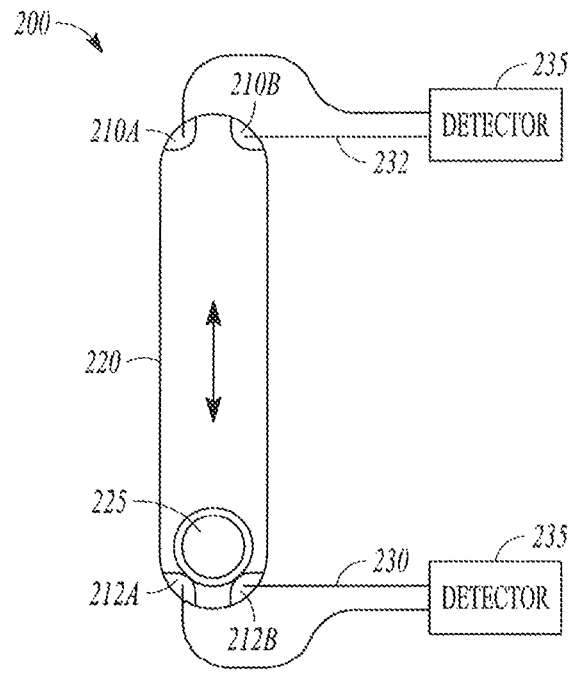
Figure 2B:
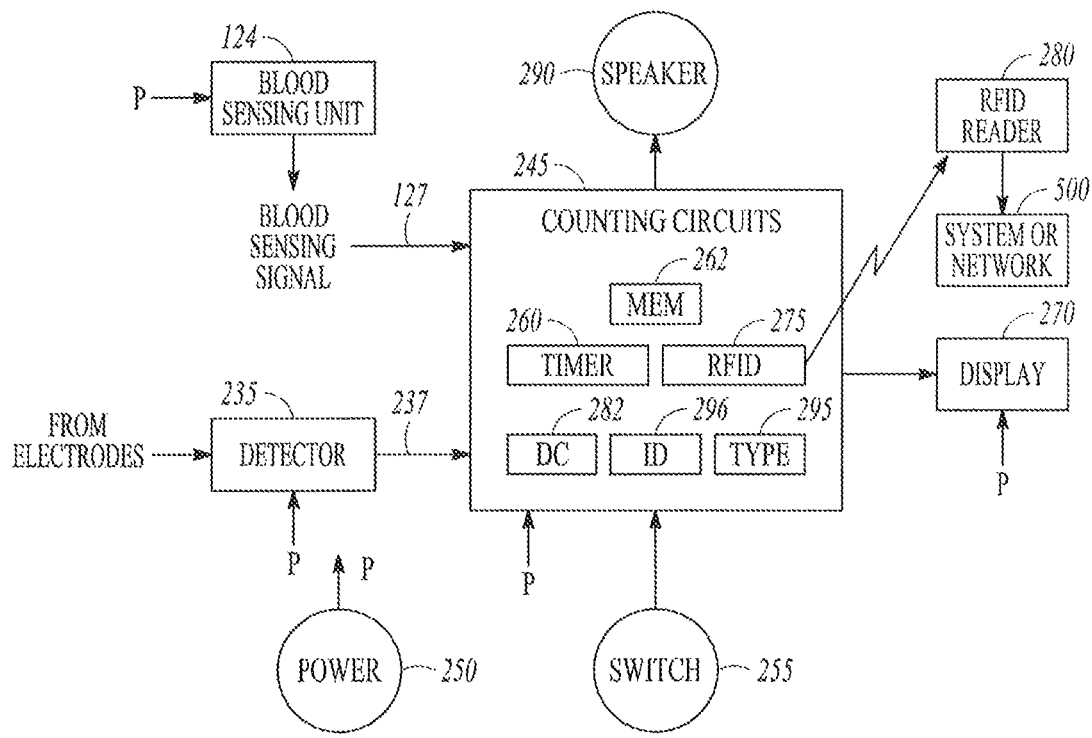

The following description should be read with reference to the drawings, in which like elements in different drawings are numbered in like fashion. The drawings, which are not necessarily to scale, depict selected embodiments and are not intended to limit the scope of the invention. Although examples of systems and methods are illustrated in the various views, those skilled in the art will recognize that many of the examples provided have suitable alternatives that can be utilized Referring now to FIGS. 1, 2A, 2B and 3, there is illustrated various embodiments of method and apparatus for collecting blood. An empty blood drawing container 100, in this example a cylindrical tube, includes anti-coagulant substance 110, and a mix detection unit 120 mounted in a housing 121 and capable of detecting, directly or indirectly, the level of mixing of blood 115 drawn from a patient into the container 100 and anti-coagulant 110. A stopper or other closure element 102 provides for closing the container 100 once the blood is collected into the container, and before the blood is mixed with the anti-coagulant 110. In one embodiment, blood 115 is drawn from a patient using a needle inserted into a vein or artery.

According to one example embodiment, the mix detection unit 120 comprises an inversion counting device 200 including a pair of contacts 210A, 210B, 212A and 212B, on each end of an enclosure 220. Enclosure 220 may, for example, be tubular in shape. A metallic element 225, such as a metallic ball or slug, is positioned and sized to travel between the opposite ends or sides of enclosure 220, alternately closing a circuit 230 or 232 between the contacts, as the container 100 is inverted. Alternatively, element 225 may be a conductive liquid, such as mercury, or a conductive granular material that can flow between ends or sides of the enclosure 220. The closing of circuit 230 or 232 is detected by electronic circuit closure detector 235 that produces an electronic signal, count or record 237 for each detection of the closing of circuit closure detector 235. Electronic counting circuits 245 counts each electronic signal, or otherwise keeps track of the number of counts detected by detector 235. Counting circuits 245 are connected to, in one embodiment, a display 270 that, under control of count circuits 245, displays a count, which is representative of the number of inversions of the container 100. A power supply 250, such as but not limited to a battery of any suitable type, supplies power P to counting circuits 245. According to one example embodiment, a switch 255 activates counting circuits 245. Switch 255 may be activated by the medical personnel withdrawing blood from a patient into collection container 100 in order to activate counting circuits 245. Switch 255 may be a mechanical switch, an electrostatic switch, or any other type of switch, but preferably a switch readily activated medical personnel handling the collection container with latex gloves or other sterile hand wear. According to one example embodiment, circuits 245 include a timer 260 that, upon activation of circuits 245, allows circuits 245 to count only those circuit closures occurring within a set period of time from activation, such as one minute, or to determine the time elapsed between each full inversion, so that the rate of inversion may be measured or recorded. The count of circuit closures, in one embodiment, is stored in a memory circuit 262, and can be read out by use of the display 270 or read out by wireless signals, such as by use of an RFID reader 280 and an RFID circuit 275, capable of wirelessly communicating with reader 280, connected directly or indirectly to the memory circuit 262. According to one example embodiment, circuits 245 are implemented using a programmable processing device such as a microprocessor with internal or external memory, and software is used to program the processing device to carry out the functions described herein with respect to circuits 245.

According to another example embodiment, the circuits 245 may be powered at all times and not require a switch, but only count and record the number of contact closures it detects if at least a predetermined number occur with a set period of time. For example, circuits 245 may be configured to only record the number of contact closures if at least at desired number of consecutive opposite end closures are recorded within a specified or desired period of time, such as at least four (4) consecutive closures within six (6) seconds. This would, for example, preclude counting most all instances of inadvertent inversions or jostling or shaking of the blood container 100, while providing a count of intended inversions or movements of the blood container by a blood handling professional for the purposes of mixing drawn blood with the anti-coagulant 110.

According to yet another example embodiment, memory circuit 262 may be used to store a desired or expected count 282 of container inversions, represented in this example embodiment by circuit closures, and counting circuits 245 can further be configured to compare the count of circuit closures to the count 282, and indicate, for example with a message or symbol displayed on display 270, that the count has been reached. Alternatively, circuits 245 may produce a sound to indicate the count has been reached, through an optional speaker element 290. A desired inversion count 282 may be obtained, for example, from the manufacturer of each particular type of blood drawing container. The manufacturer typically enumerates the number of inversions that must be performed for each type of blood drawing tube they distribute.

In still another embodiment, either or both the type 295 of blood collection container, and a unique serial number or identification (ID) 296 for the container, are also stored in the memory circuit 262, for later recall and display on display 270 or electronic output to a reading device or computing apparatus.

According to other example embodiments, the counting apparatus or mechanism may take many other forms, and the blood collection technology described herein is not limited to any particular counting mechanism. For example, the movement of the movable element may be optically detected with an optical sensor in each end of the tube, wherein a light (visible or not visible) beam shone from an optical emitter is received on a corresponding optical light detector and the beam is broken by the presence of the moving element. In the alternative, many other mechanical, optical or other mechanisms may be provided to count inversions or mixing action. In another form, the counting apparatus may be formed from micro-mechanical components. Or, an integrated circuit accelerometer may be provided, wherein counting circuits 245 is configured to receive accelerometer signals and determine the changing orientation of the collection container, and derive a count of inversions or mixing motions therefrom.

According to still another example embodiment, unit 120 includes a blood sensing unit 124 (FIG. 2B), for example employing optical sensing elements, and circuits 245 include an input that is activated by a signal 127 generated by unit 124 when blood flows into the container. Upon detection of blood in the container 100, circuits 245 are activated to count the number of inversions that occur in a set amount of time after detection of the blood. For example, the sensing unit 124 may detect a change in the ambient level of light in the blood collection container due to the receipt of blood into the container. However, any other suitable approach to detecting the presence of blood may also be used. By use of this mechanism, the unit 120 is capable of determining how soon after blood is received in the container 100 that the mixing occurs.

Figure 3:
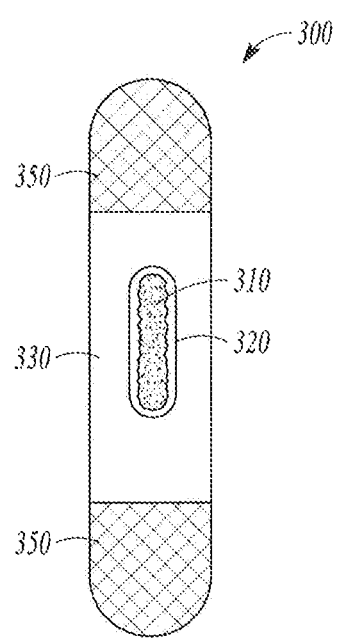

According to still another example embodiment, apparatus 120 may use one or more chemical reactions to detect the level of mixing, such as shown in FIG. 3. As illustrated in FIG. 3, an apparatus 300 may include solution 310 contained inside a breakable capsule 320 inside a flexible walled tube 330. Capsule 320 may be broken by medical personnel by applying pressure on the outside surface of the wall of tube 330 and in turn capsule 320 to break the capsule, which may be formed of thin glass or plastic or other material. Chemical elements or compounds 350 on each end of a tube 330 react with solution 310 released from capsule 320, and in one example embodiment, turn color based on the level of mixing of solution 310 with elements or compounds 350. If elements or compounds 350 on both end of the tube attain the desired color the proper mixing level would be evidenced.

According to still other embodiments of the present technology, the mix detection unit 120 may be operatively coupled or attached to the blood collection container in a variety of different ways. In one example embodiment, unit 120, and more particularly the housing 121 of unit 120, may be mounted outside the collection container, either in a removable fashion or in a permanent fashion, using a fastening mechanism 122. Mechanism 122 may be, for example in one example embodiment, an adhesive that fixes, through adhesive action, the housing 121 to container 100. In another embodiment, mechanism 122 may be a sleeve 123 that wraps around the outside perimeter of container 100, to hold housing 121 in place adjacent container 100. Or, a Sleeve 123 may be elastic or inelastic, and provide for elastically encircling the container 100 or providing an interference fit with the container 100. Alternatively, container 100 may include a mechanical or topographical feature on its outside surface to allow mechanism 122 to snap on or clip onto housing 121. In operation, accordingly, housing 121 would be disposed of with container 100 should container 100 be disposed of, or it could be sterilized with container 100 if container 100 were to be reused. Alternatively, housing 121 could be removed from attachment to container 100 and disposed of or sterilized and reset by electronic means for reuse with a new or recycled container 100.

Thus, as described above, there is provided a number of methods for collecting blood, including a method that provides for filling a blood collection container with blood, inverting the blood collection container by hand to mix the blood with an anti-coagulant, and viewing or listening to an indication generated by a mix detection device attached to the blood collection container, wherein the indication provides information about the appropriate amount of mixing for the blood According to one example embodiment (FIG. 2B), the count of inversions (or other indication of mixing) is read or transmitted, for example using the above-mentioned RFID mechanism, or any other wireless mechanism such as near-field, Blue Tooth® or other wireless transmissions, to a central device or computing system, or network 500, optionally along with the serial number of the blood container or type of blood container, as either or both may be optionally stored and read. The blood mixing practices of phlebotomists can thus be continually or intermittently assessed. This count could also be available in the central laboratory where the blood specimens are processed and distributed. Specimens that were not mixed might be pulled of the line and not analyzed. Research could correlate the mixing to deficiencies in laboratory testing. Such research would be useful in developing newer blood containers and tubes. The end product of such a counter would result in improved patient safety, higher efficiency in phlebotomy and total decreased costs to the health care system. Furthermore, having records of mixing compliance would be useful in training new phlebotomists.

Thus, as described above, the present technology provides a number of benefits. The most direct benefit is an opportunity to improve compliance with blood mixing requirements, as phlebotomists' efforts to reliably mix the blood specimen will be made more measurable. Furthermore, with improved compliance for mixing, time will be saved that is now spent by laboratory personnel attempting to visualize clots within anti-coagulated specimens and preventing their introduction into today's blood analyzers. Furthermore, by improving the mixing, fewer suboptimal specimens will be analyzed by the laboratory, and many negative ramifications may be avoided, such as compromised laboratory instruments, delayed or incorrect diagnoses, increased costs of follow-up patient investigation and associated patient risks.

The embodiments and examples set forth herein are presented to best explain the present technology and its practical application and to thereby enable those skilled in the art to make and utilize the technology. Those skilled in the art, however, will recognize that the foregoing description and examples have been presented for the purpose of illustration and example only. Other variations and modifications of the present technology will be apparent to those of skill in the art, and it is the intent of the appended claims that such variations and modifications be covered.

The description as set forth is not intended to be exhaustive or to limit the scope of the technology. Many modifications and variations are possible in light of the above teaching without departing from the scope of the following claims. It is contemplated that the use of the present technology can involve components having different characteristics. It is intended that the scope of the present technology be defined by the claims appended hereto, giving full cognizance to equivalents in all respects.

The invention claimed is:

1. A method comprising:
a phlebotomist extracting blood from a patient;
the phlebotomist adding the extracted blood to a blood collection container;
the phlebotomist repeatedly inverting the blood collection container by hand to mix the blood with an anti-coagulant or pro-coagulant in the blood collection container;
a mix detection device attached to the blood collection container counting, using a counting circuit electrically connected to an accelerometer, the number of inversions performed by the phlebotomist as the phlebotomist repeatedly inverts the blood collection container; and
the phlebotomist listening to an indication generated by a speaker of the mix detection device, wherein the indication provides information indicating the number of counted inversions.

2. A method according to claim 1 wherein the phlebotomist viewing or listening to the indication generated by the mix detection device includes the phlebotomist listening for an audible indication from the mix detection unit that the blood and the anti-coagulant or pro-coagulant in the blood collection container are sufficiently mixed.

3. A method according to claim 1 further comprising the phlebotomist viewing a visual indication generated by a display of the mix detection device the visual indication indicating an extent to which the blood and the anti-coagulant or pro-coagulant in the blood collection container are mixed.

4. A method according to claim 1 further comprising recording in a memory, an indication of whether the blood container was sufficiently mixed, and refraining from analyzing the blood in the blood container if the indication indicates the blood is insufficiently mixed.

5. A method according to claim 1 further comprising the mix detection device attached to the blood collection container providing information about an expected number of inversions for the blood collection container in a specified amount of time.

6. A method according to claim 1 wherein the mix detection device counting the number of inversions performed includes a metallic element completing a circuit between two contacts and a counting circuit keeping track of the number of circuit closures.

7. A method according to claim 6 wherein the phlebotomist viewing or listening to an indication generated by the mix detection device attached to the blood collection container includes the phlebotomist viewing a display of the number of inversions on the blood collection container.

8. A method according to claim 5 the mix detection device attached to the blood collection container providing information about the expected number of inversions for the blood collection container in a specified amount of time includes the mix detection device comparing the expected number inversions to the counted the number of inversions and the mix detection device providing a sound, or a symbol on the display, that the expected count has been reached.

9. A method according to claim 1 further comprising the mix detection device determining, by a sensor of the mix detection device, how soon after blood is received in the blood collection container that the phlebotomist inverts the blood collection container.

10. A method according to claim 1 further comprising transmitting the counted number of inversions to a computer network.

11. A method according to claim 10 further comprising monitoring the mixing habits of the phlebotomist by assessing the transmitted number of inversions.

* * * * *